United States Patent [19]
Ek et al.

[11] Patent Number: 6,086,608
[45] Date of Patent: *Jul. 11, 2000

[54] SUTURE COLLET

[75] Inventors: Steven W. Ek, Bolton, Mass.; Kenneth K. Thompson, Palm Harbor; Randall D. Ross, Largo, both of Fla.; Jose Lizardi, Franklin, Mass.

[73] Assignee: Smith & Nephew, Inc., Andover, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/783,126

[22] Filed: Jan. 14, 1997

Related U.S. Application Data

[63] Continuation-in-part of application No. 08/605,767, Feb. 22, 1996.

[51] Int. Cl.$^7$ ........................................... A61B 17/04
[52] U.S. Cl. ................................. 606/232; 606/72
[58] Field of Search .................... 606/72, 73, 75, 606/139, 144, 145, 148, 232

[56] References Cited

U.S. PATENT DOCUMENTS

| | | |
|---|---|---|
| 2,665,597 | 1/1954 | Hill . |
| 3,541,591 | 11/1970 | Hoegerman ........................... 128/335 |
| 3,664,345 | 5/1972 | Dabbs et al. .......................... 128/335 |
| 3,665,560 | 5/1972 | Bennett et al. . |
| 3,845,772 | 11/1974 | Smith . |
| 3,910,281 | 10/1975 | Kletschka et al. . |
| 3,976,079 | 8/1976 | Samuels et al. ....................... 128/335 |
| 4,235,238 | 11/1980 | Ogiu et al. ............................. 128/334 |
| 4,287,807 | 9/1981 | Pacharis et al. . |
| 4,291,698 | 9/1981 | Fuchs et al. ........................... 128/335 |
| 4,473,102 | 9/1984 | Ohman et al. . |
| 4,532,926 | 8/1985 | O'Holla ................................. 128/334 |
| 4,573,844 | 3/1986 | Smith . |
| 4,669,473 | 6/1987 | Richards et al. ....................... 128/334 |
| 4,719,671 | 1/1988 | Ito et al. . |
| 4,741,330 | 5/1988 | Hayhurst ................................. 128/92 |
| 4,744,353 | 5/1988 | McFarland ............................. 128/92 |

(List continued on next page.)

FOREIGN PATENT DOCUMENTS

| | | |
|---|---|---|
| 0 270 704 A1 | 6/1988 | European Pat. Off. . |
| 0 340 159 A1 | 3/1989 | European Pat. Off. . |
| 0 409 364 A2 | 1/1991 | European Pat. Off. . |
| 0 502 509 A1 | 9/1992 | European Pat. Off. . |
| 0 574 707 A1 | 12/1993 | European Pat. Off. . |
| 0 591 991 A2 | 4/1994 | European Pat. Off. ........ A61B 17/00 |
| 2 682 867 | 4/1993 | France . |
| WO 95/32670 | 7/1995 | WIPO . |
| WO 95/29637 | 11/1995 | WIPO . |

OTHER PUBLICATIONS

Innovasive Devices, Inc., Product Information Sheet, ROC Fastener System.

*Primary Examiner*—Michael Buiz
*Assistant Examiner*—Daphna Shai
*Attorney, Agent, or Firm*—Fish & Richardson P.C.

[57] ABSTRACT

A suture securing device includes an outer member with a suture receiving passage and an inner member configured for progressive insertion within the suture receiving passage and engagement with the outer member in any one of a plurality of locked positions to secure a suture between the inner member and the outer member. The suture receiving passage includes a threaded portion and the inner member includes a ridge for progressive engagement with threads of the threaded portion. A suture securing cartridge includes a sleeve having an axial bore with the outer member disposed in the bore at a distal end of the sleeve, the inner member disposed in the bore proximally of the outer member, and a carrier which engages the inner member to align the inner member with the suture receiving passage.

34 Claims, 17 Drawing Sheets

U.S. PATENT DOCUMENTS

| | | |
|---|---|---|
| 4,744,793 | 5/1988 | Parr et al. . |
| 4,750,492 | 6/1988 | Jacobs ................................ 128/335 |
| 5,078,731 | 1/1992 | Hayhurst .............................. 606/232 |
| 5,224,946 | 7/1993 | Hayhurst ................................ 606/72 |
| 5,268,001 | 12/1993 | Nicholson et al. ..................... 606/72 |
| 5,282,832 | 2/1994 | Toso et al. . |
| 5,324,308 | 6/1994 | Pierce .................................. 606/232 |
| 5,336,240 | 8/1994 | Metzler et al. ....................... 606/232 |
| 5,423,860 | 6/1995 | Lizardi et al. ........................ 606/232 |
| 5,458,601 | 10/1995 | Young, Jr. et al. . |
| 5,464,427 | 11/1995 | Curtis et al. ......................... 606/232 |
| 5,480,403 | 1/1996 | Lee et al. . |
| 5,486,197 | 1/1996 | Le et al. . |
| 5,573,548 | 11/1996 | Nazre et al. ......................... 606/232 |
| 5,584,835 | 12/1996 | Greenfield ............................. 606/72 |
| 5,630,824 | 5/1997 | Hart ..................................... 606/139 |
| 5,643,321 | 7/1997 | McDevitt . |
| 5,649,963 | 7/1997 | McDevitt . |

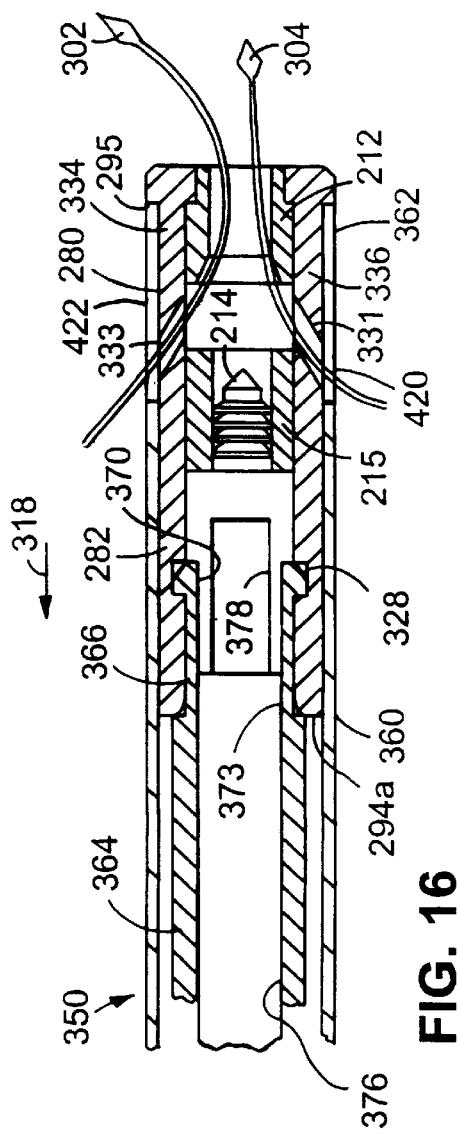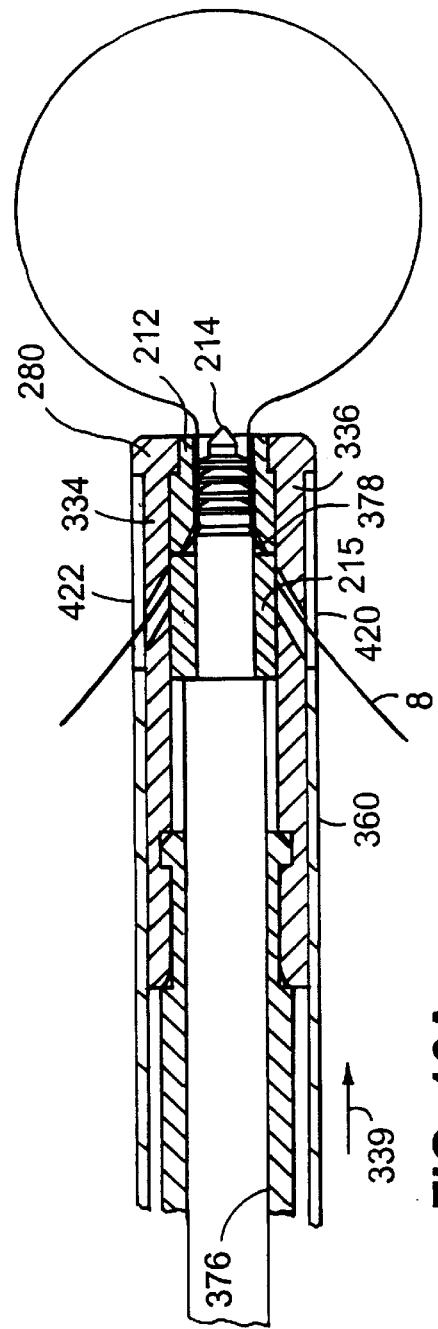

SUTURE COLLET

CROSS REFERENCE TO RELATED APPLICATION

This application is a continuation-in-part of application Ser. No. 08/605,767, filed Feb. 22, 1996.

BACKGROUND OF THE INVENTION

This invention relates to suture fastening.

One traditional method of fastening suture is simply by tying a knot in the suture. Alternatively, a suture clamp may be used. In a typical suture clamp, the suture is positioned between an open pair of arms which are then pivoted closed to capture the suture between them.

SUMMARY OF THE INVENTION

A suture securing device includes an outer member with a suture receiving passage and an inner member configured for progressive insertion within the suture receiving passage and engagement with the outer member in any one of a plurality of locked positions to secure a suture between the inner member and the outer member.

Preferred embodiments may include one or more of the following features.

The suture receiving passage includes a threaded portion and the inner member includes a ridge for progressive engagement with threads of the threaded portion. The inner member includes a plurality of ridges for progressive engagement with the threads of the outer member. The inner member defines a long axis and a distal surface of the ridge is inclined relative to the long axis to slide past the threads during insertion, and a proximal surface of the ridge is oriented perpendicular to the long axis to lockingly engaging the threads when the inner member has been inserted within the suture receiving passage by a desired amount.

Preferably, the proximal end of the suture receiving passage tapers distally from a wider diameter to a smaller diameter, and a distal end of the inner member is conically shaped. The taper and the conical shape aid in the insertion of the inner member within the suture receiving passage.

In another embodiment, a suture securing cartridge includes a sleeve having an axial bore and a suture securing device with an outer member disposed in the bore at a distal end of the sleeve and an inner member disposed in the bore proximally of the outer member. The inner member being configured for insertion into a suture receiving passage in the outer member.

A carrier is disposed in the bore proximally of the outer member and the carrier engages the inner member to align the inner member with the suture receiving passage. The carrier defines an opening and the inner member is disposed in the opening.

A proximal end of the sleeve is configured to receive an actuator for moving the inner member into the suture receiving passage.

The sleeve has a distal clamp for selectively preventing the outer member from exiting the bore in a distal direction. The distal clamp includes a resilient arm which is outwardly flexible to permit the outer member to exit the bore in the distal direction.

The sleeve includes an inclined aperture extending through a wall of the sleeve and a suture threader extends through the inclined aperture and through the suture receiving passage. The suture threader includes a cap covering an open end of the bore at a proximal end of the sleeve.

In another embodiment, a suturing apparatus includes the suture securing cartridge and a drive tool having an outer sheath which fits over the sleeve, an intermediate tube which engages the sleeve to secure the cartridge to the drive tool, and a movable element located within the intermediate tube for progressively inserting the inner member into the passage of the outer member.

Preferably, the sleeve has a circumferential groove in the bore, and the intermediate tube has a grasper which engages the groove to secure the cartridge to the drive tool.

Another aspect of the invention features a method of securing a suture. The method includes threading a suture through a passage in an outer member, and progressively inserting an inner member into the outer member to engage the inner member with the outer member in any one of a plurality of locked positions to secure the suture between the inner member and the outer member.

In another embodiment, a method of using a suture securing device includes providing a preassembled suture securing cartridge; inserting the preassembled suture securing cartridge into a drive tool; and advancing a movable element of the drive tool to progressively insert the inner member into the passage.

We have found that the holding power of suture securing device is substantially greater than that of a standard open surgical knot.

Other features and advantages of the invention will be apparent from the following detailed description, and from the claims.

BRIEF DESCRIPTION OF THE DRAWINGS

FIGS. 16–16B show the drive tool in use with the suture collet; and

DESCRIPTION OF THE PREFERRED EMBODIMENTS

Figure 1:
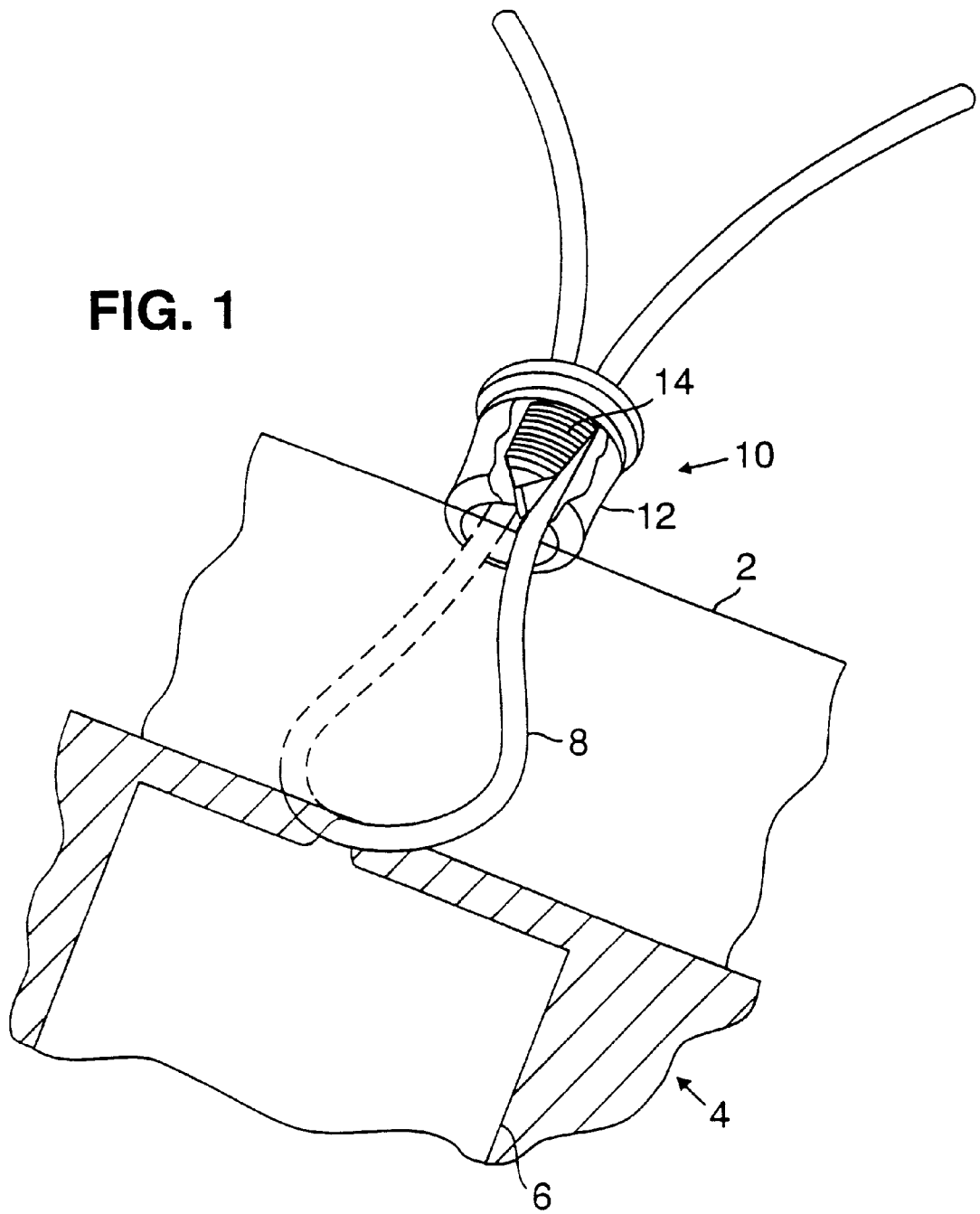
FIG. 1 shows a suture collet for securing suture.

Referring to FIG. 1, a suture collet 10 is used in place of conventional securing techniques (e.g., knot tying) to secure a suture 8 in place. Suture collet 10 can be used in a wide variety of applications—in the operation shown schematically in FIG. 1, suture collet 10 clamps a loop of suture 8 in place between a ligament 2 and a bone 4 (suture 8 is attached to bone 4 by a suture anchor 6 or other suitable device). As discussed in more detail below, suture collet 10 includes an outer locking ring 12 and an inner locking pin 14 each of which include inclined clamping surfaces which progressively constrict suture openings (and thus securely fasten suture 8 in place) when pin 14 is inserted into ring 12.

Figure 2:
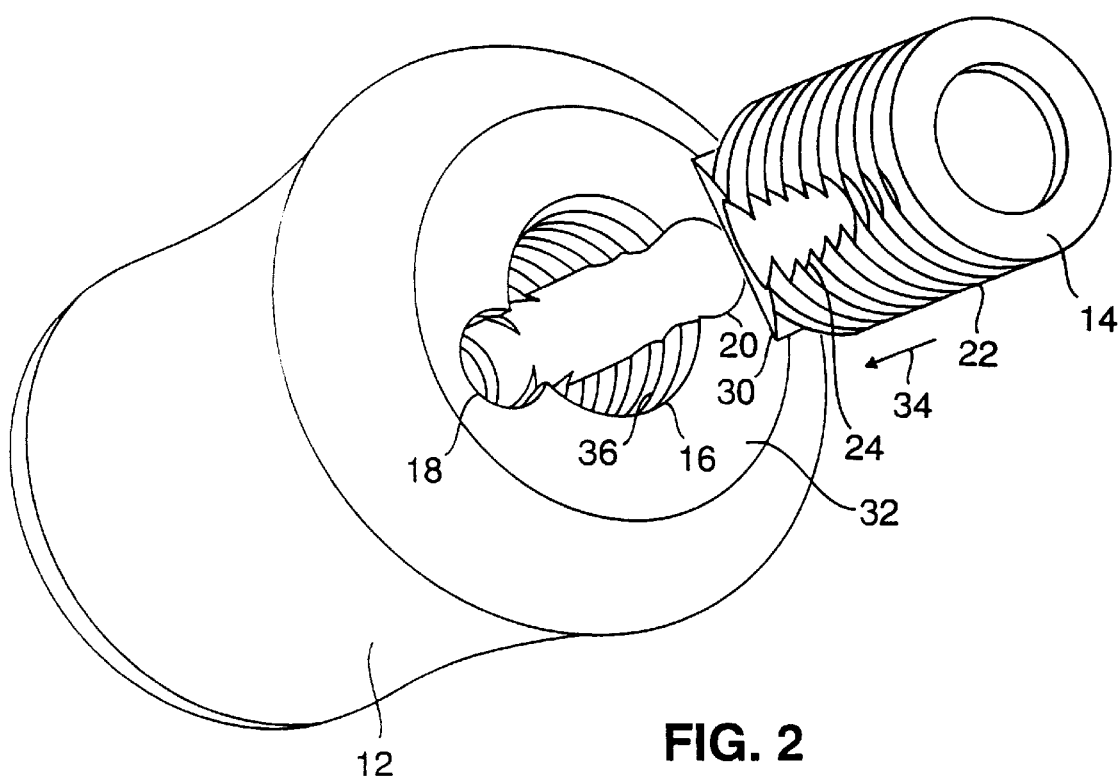
FIG. 2 is a perspective view of the suture collet of FIG. 1.

Referring to FIG. 2, suture collet 10 is shown in more detail. Ring 12 includes an axially-oriented cylindrical bore 16. A portion of the interior surface of ring 12 which defines bore 16 is threaded 36. Pin 14 is generally cylindrical in shape and is sized to enter bore 16. A portion of the exterior surface of pin 14 includes a series of axially spaced ridges 22 for lockingly engaging threads 36 in a ratchet-like manner when pin 14 is inserted into bore 16 and secure ring 12 and pin 14 together.

Ring 12 includes a pair of axially oriented, inclined tunnels 18, 20 which intersect bore 16. A pair of inclined, concave surfaces 24, 26 (FIG. 4A) on the exterior of pin 14 are circumferentially aligned with tunnels 18, 20 when pin 14 is inserted into ring 12 to respectively define a pair of suture receiving openings 52, 53 (FIG. 5) through which suture 8 (FIG. 1) is passed. As discussed in more detail below, as pin 14 is inserted axially into bore 16 (in the direction of arrow 34, FIG. 2), inclined surfaces 24, 26 slide axially with respect the inclined surfaces which define tunnels 18, 20, thereby progressively constricting suture receiving openings 52, 53 and securely clamping suture 8 therein. The inclined nature of these clamping surfaces provides a significant mechanical advantage during insertion so that the clamping force applied to suture 8 exceeds the force used to insert pin 14 into ring 12.

Figure 3:
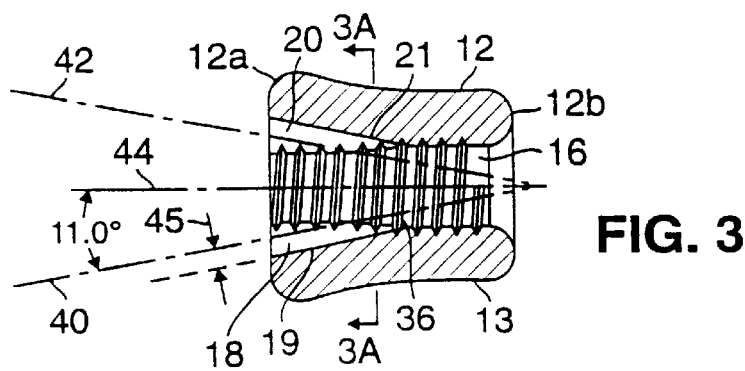
FIG. 3 is a side view of an outer member of the suture collet of FIG. 1.
Figure 3A:
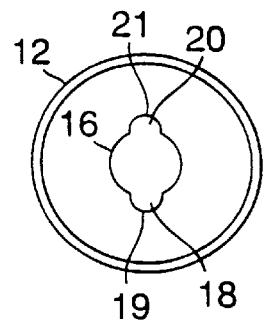
FIG. 3A is an end view of the outer member of FIG. 3, taken along lines 3A—3A.

Referring to FIGS. 3 and 3A, ring 12 is shown in more detail. Threaded bore 16 extends completely through ring 12, from proximal end 12a to distal end 12b, along a longitudinal central axis 44 of ring 12. Tunnels 18, 20 are diametrically opposed (i.e., spaced by 180 degrees) at the periphery of bore 16 and extend axially from ring proximal end 12a along axes 40, 42, respectively. Tunnels 18, 20 interrupt threads 36 and are respectively defined by inclined, concave smooth surfaces 19, 21, (FIG. 3A) which are spaced from axes 40, 42 by a radius 45 of, e.g., 0.012 inches.

Tunnel axes 40, 42 are inclined with respect to longitudinal axis 44, and thus tunnels 18, 20 decrease in cross-sectional area (from a maximum at proximal end 12a) as they extend axially along bore 16. The angle at which tunnels 18, 20 are inclined is between about 5° and 20°, and preferably is 11°. Each tunnel 18, 20 ends approximately mid-way between proximal and distal ends 12a, 12b. The walls 13 of ring 12 are relatively constant in thickness along the length of ring 12. Thus, proximal end 12a has a flared outer diameter with respect to distal end 12b.

Figure 4:
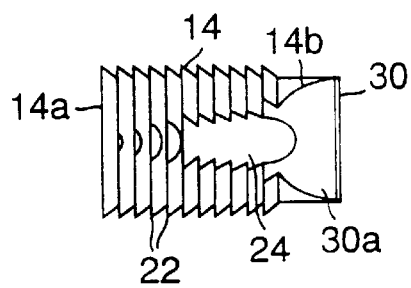
FIGS. 4 and 4A are side views (rotated by 90° with respect to each other) of an inner member of the suture collet of FIG. 1.
Figure 4A:
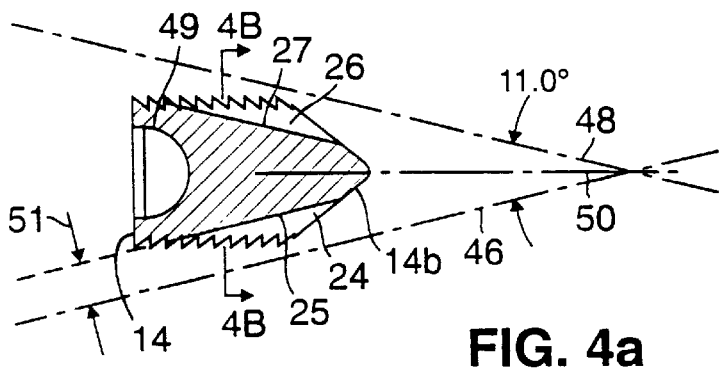
Figure 4B:
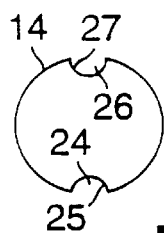
FIG. 4B is an end view of the inner member, taken along lines 4B—4B of FIG. 4A.

Referring to FIGS. 4–4B, the circumferentially oriented ridges 22 of pin 14 are axially spaced along pin 14 between proximal end 14a and distal end 14b. The leading (distal) surfaces of ridges 22 inclined (e.g., at 45 degrees) to slide past threads 36 of ring 12 during insertion, and the trailing (proximal) surfaces of ridges 22 are transversely oriented to lockingly engaging threads 36 when pin 14 has been inserted by the desired amount. A pair of diametrically opposed tunnels 24, 26 which interrupt ridges 22 are formed in the exterior surface of pin 14. Tunnels 24, 26 are respectively defined by concave inclined surfaces 25, 27 (FIG. 4A) which are respectively spaced from tunnel axes 46, 48 by a radius 51 of, e.g., 0.012 inches.

Tunnel axes 46, 48 are inclined with respect to the longitudinal axis 50 of pin 14. The inclined angle is, e.g., between about 5° and 20°, and preferably is 11°; note that in the embodiment shown, tunnels 24, 26 are inclined at the same angle as ring tunnels 18, 20, but they needn't be. Accordingly, tunnels 24, 26 taper from a maximum cross-sectional area at their distal end (near pin distal end 14b) and terminate near proximal end 14a.

Distal end 14b of pin 14 is noncylindrical and includes a pair of flat, beveled surfaces 30a (only one of which is shown in FIG. 4) which are tapered together and meet along a straight edge 30 at the extreme distal tip of pin 14. As discussed below, beveled surfaces 30a help guide suture 8 into suture receiving openings 52, 53 when pin 14 is inserted into ring 12. Pin 14 can optionally include a proximal opening 49 for receiving a drive pin.

The overall size of suture collet 10 with pin 14 inserted into ring 12 corresponds approximately to the size of three successive throws of a suture knot. For example, ring 12 is 0.15 inches long and has a maximum outer diameter of 0.14 inches; pin 14 is only 0.095 inches long (and thus can fit entirely within ring 12) and has a maximum outer diameter of 0.045 inches. Ring 12 and pin 14 can be made from a non-absorbable material such as polyacetal available from M. Holland Co., Northbrook, Ill., or a bio-absorbable material, such as Maxon, a polyglyconate, available from Davis & Geck.

Figure 5:
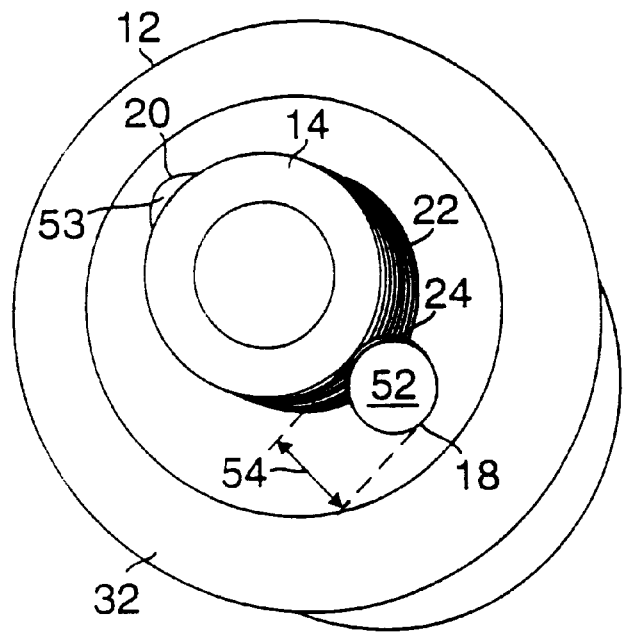
FIG. 5 is a perspective view of the suture collet with the inner and outer members interconnected in a first position.
Figure 5A:
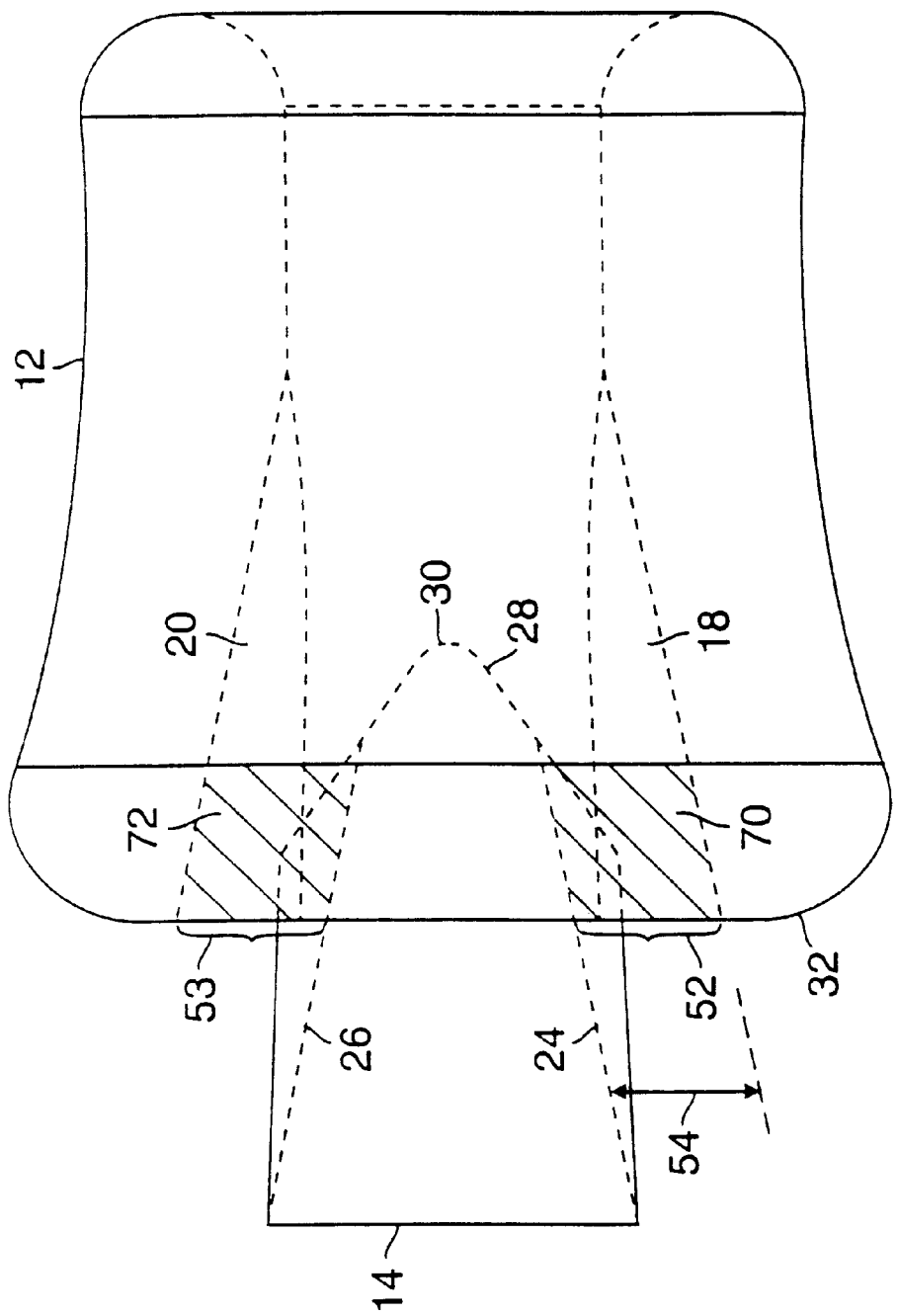
FIG. 5A is a side view of the suture collet of FIG. 5.

Referring to FIGS. 5 and 5A, suture collet 10 clamps suture as follows. After suture (not shown) has been passed through bore 16 (a tool and procedure for doing so are described below) and positioned within tunnels 18, 20, pin 14 is inserted into ring 12 so that tunnels 18, 24 are aligned (to define suture receiving opening 52) and tunnels 20, 26 are aligned (which defines suture receiving opening 53). Beveled surfaces 30a of pin distal end 14b help guide the suture into tunnels 24, 26 as pin 14 enters ring 12. With pin 14 partially inserted into ring 12 in the position shown in FIGS. 5 and 5A, suture receiving openings 52 and 53 are circular in cross section and form elongated, cylindrical channels 70 and 72 between ring 12 and pin 14. At this point, channels 70, 72 have a diameter 54 of about 0.024 inches. The radius of the tunnels, and thus the diameter of the channels in the position shown in FIGS. 5 and 5A, is selected to correspond to a particular size of suture, the suture in the illustrated embodiment being a #2 suture with a diameter of about 0.020 to 0.023".

Figure 6A:
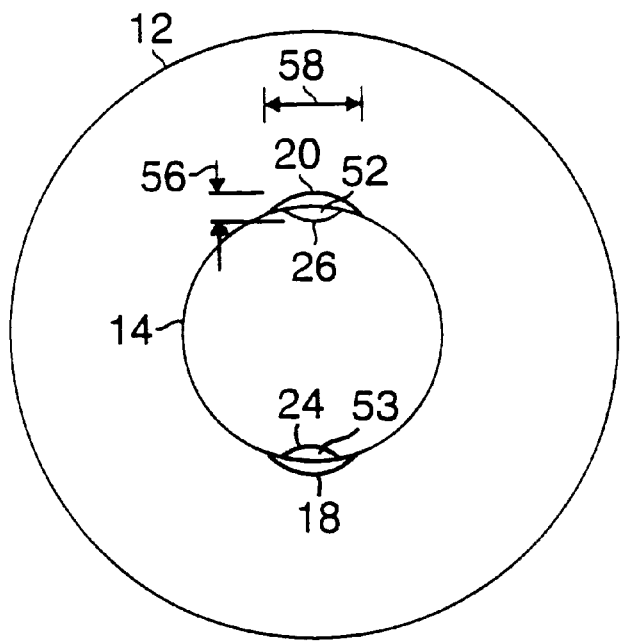
FIG. 6A is an end view of the suture collet of FIG. 6, taken along lines 6A—6A.
Figure 6:
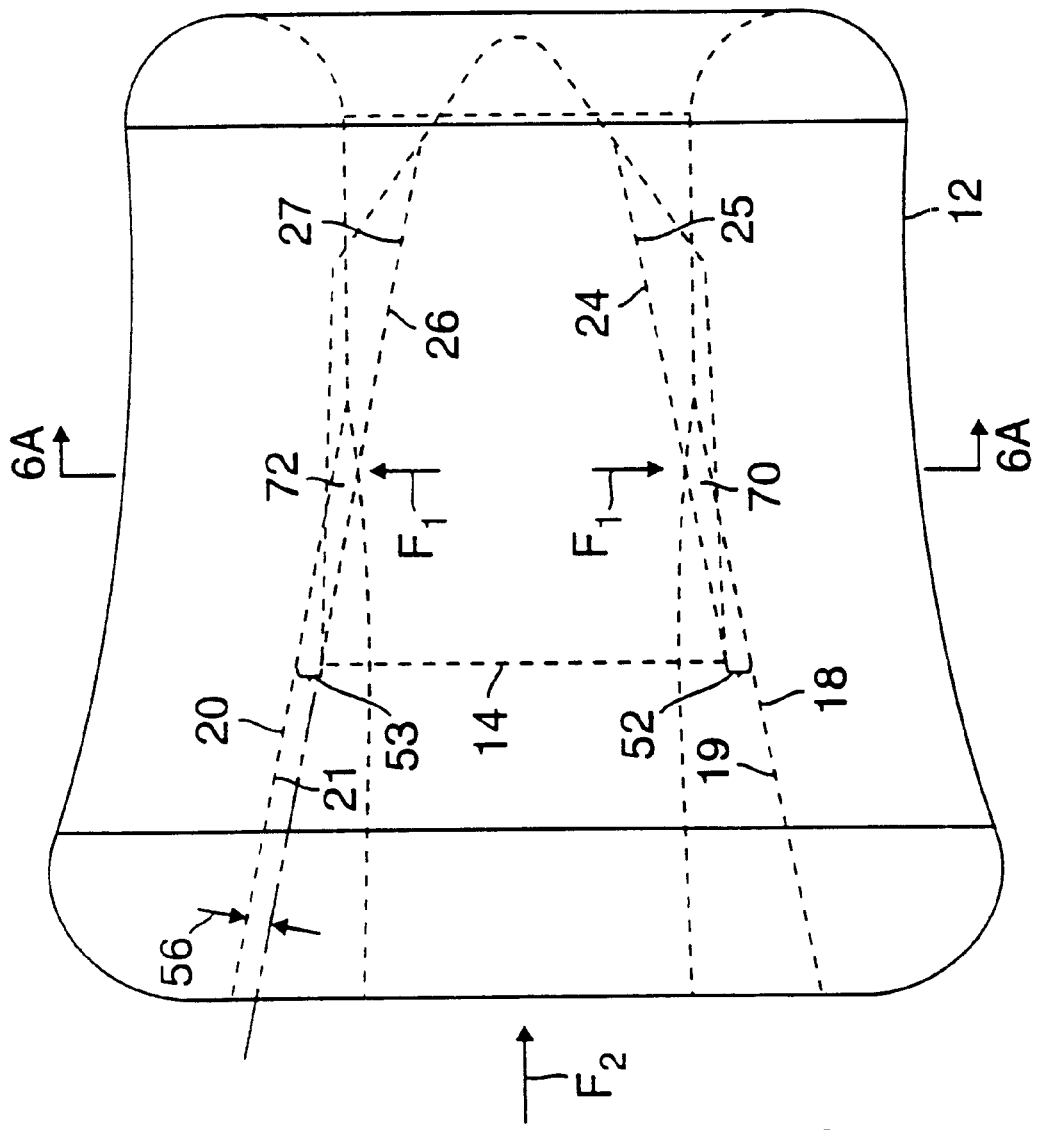
FIG. 6 is a side view of the suture collet in a second interconnected position.

Referring also to FIGS. 6 and 6A, as pin 14 is progressively advanced into ring 12, pin inclined surfaces 25, 27 slide axially with respect to ring inclined surfaces 19, 21, respectively, thereby progressively constricting suture receiving openings 52, 53 (and channels 70, 72 formed thereby) and clamping the suture (not shown) therein. Openings 52, 53 lose their circular cross section and become progressively more oblong (FIG. 6A) as pin 14 is inserted still further. With pin 14 fully inserted (FIG. 6), suture receiving openings 52, 53 have a short dimension 56 of about 0.004" and a long dimension 58 of about 0.015".

This progressive constriction of suture receiving openings 52, 53 compresses the suture thread located therein to securely clamp the suture in place therein. Similarly to the action of a door wedge—which produces a strong force at right angles to the direction of movement as the wedge is inserted under a door—the movement of inclined surfaces 25, 27 of pin 14 toward inclined surfaces 19, 21 of ring 12 exerts a strong radial force F1 (FIG. 6) on the suture thread. The mechanical advantage gained with the inclined surfaces results in radial force F1 being greater than the axial force F2 required to insert pin 14 into ring 12.

Figure 7:
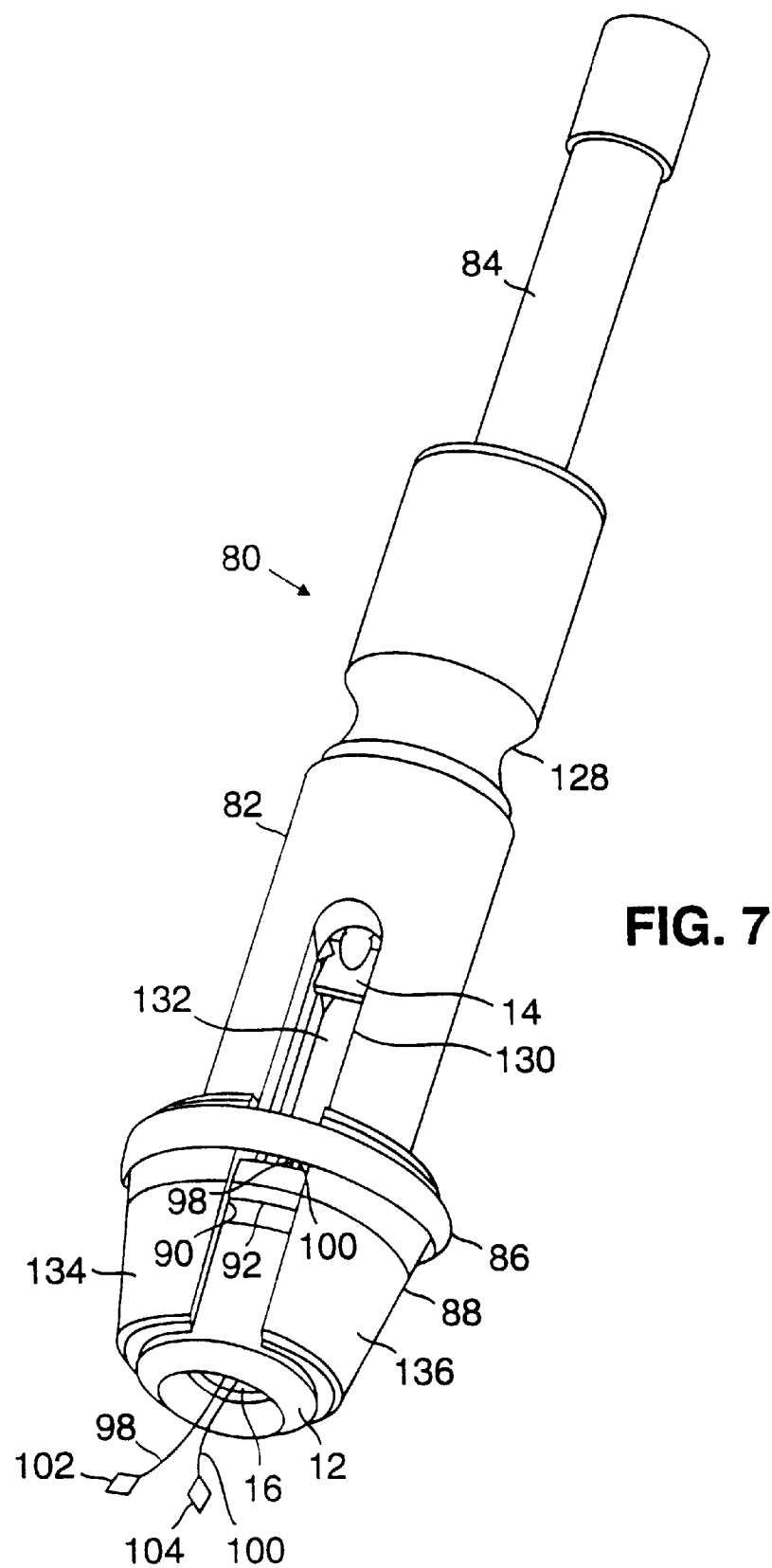
FIG. 7 shows a drive tool for use with the suture collet of FIG. 1.
Figure 8:
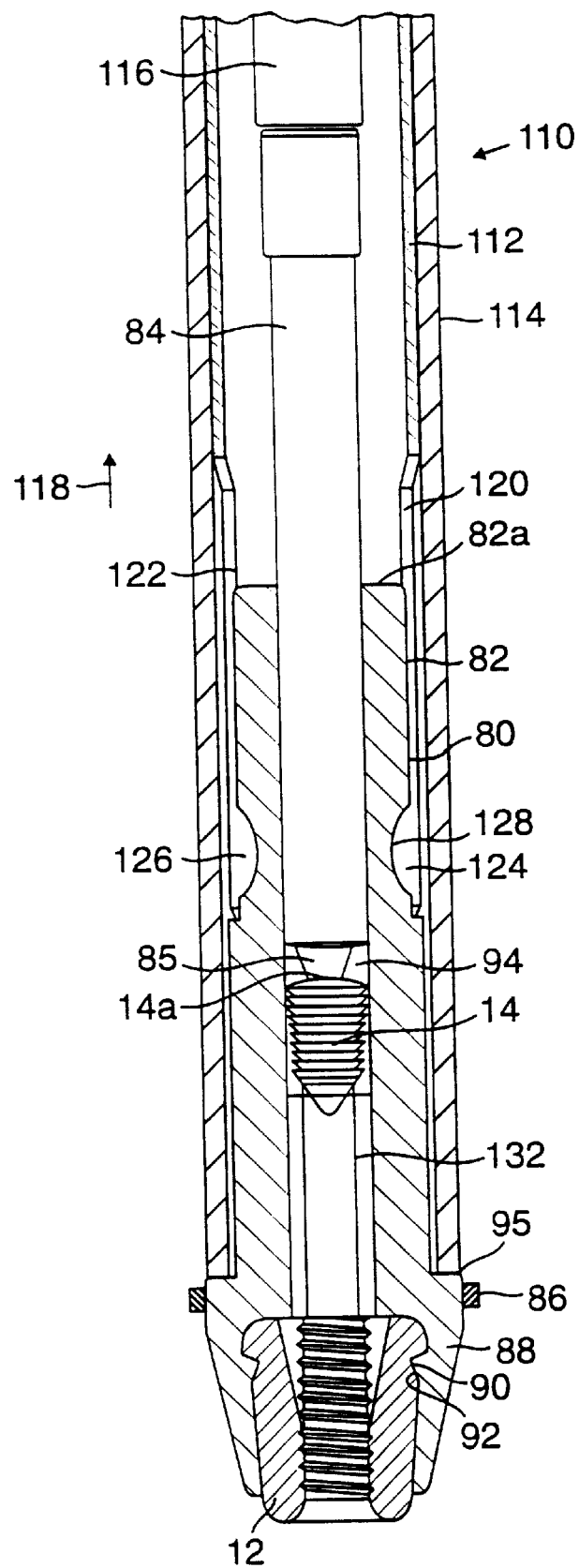
FIGS. 8–8C show the drive tool in use with the suture collet.

FIGS. 7 and 8 illustrate instruments which can be used to emplace suture collet 10 in the body and insert pin 14 into ring 12 to clamp suture in place in the manner discussed above. A cartridge 80 which carries ring 12 and pin 14 is shown in FIG. 7. Cartridge 80 includes a hollow sleeve 82 the distal end of which is provided with a pair of axial slots 130, 132 to define a pair of resilient arms 134, 136 which form a clamp 88 to hold suture collet ring 12 in place therebetween. Arms 134, 136 are curved to conform to the shape of suture collet ring 12, and interior lips 90 on arms 134, 136 snap fit (due to the resiliency of arms 134, 136) within a circular groove 92 in ring 12 (groove 92 is not shown in FIGS. 1–6A and may be omitted).

Sleeve 82 has a generally cylindrical exterior surface, but includes a reduced diameter waist proximally of the proximal ends of slots 130, 132 for purposes to be described. The outer diameter of arms 134, 136 is enlarged relative to that of the remainder of sleeve 82, such that a shoulder 95 is defined, also for purposes to be discussed. As shown in FIG. 8, an axial passage 94 extends through sleeve 82. Pin 14 is supported within passage 94 by an interference fit with the walls of passage 94 to maintain pin 14 axially spaced from ring 12 until it is to be inserted into ring 12.

Cartridge 80 also includes a plunger 84 which is slidable within and is approximately the same diameter as passage 94. The proximal end of plunger 84 protrudes from the proximal end 82*a* of sleeve 82. The distal end 85 of plunger 84 is cone shaped and engages pin proximal end 14*a*. The cone shaped distal end 85 acts to center the drive load applied by plunger 84 on pin 14, and, if pin 14 includes opening 49, the cone shaped distal end is received in the opening.

A suture threader which includes a collar 86 slidable over an outer tube 114 of a delivery system 110 is used to thread suture through ring 12 during operation. Collar 86 is connected to the proximal ends of a pair of suture threader wires 98, 100 which respectively pass through slots 130, 132 and into passage 94. With collar 86 held in the position shown in FIG. 7 by an interference fit over clamp 88, the free ends of wires 98, 100 pass through bore 16 of suture collet ring 12 and terminate in a pair of threading loops 102, 104, respectively.

Referring in particular to FIG. 8, delivery system 110 is used to convey cartridge 80 (pre-loaded with ring 12 and pin 14) to the surgical site. Delivery system 110 includes a hollow grasper 112 coaxially disposed within a slidable outer tube 114. Grasper 112 has a pair of flexible arms 120, 122 the distal ends 124, 126 of which are configured to fit within narrow waste 128 of sleeve 82. An actuator 116 is slidable within grasper 112 to engage and actuate cartridge plunger 84.

Cartridge 80 is inserted into delivery system 110 by retracting outer tube 114 distally (in the direction of arrow 118) to expose grasper ends 124, 126 and allow them to flex outwardly. Cartridge 80 is then inserted between grasper arms 120, 122, until ends 124, 126 reach and snap fit within waist 128. Outer tube 114 is then returned to the position shown in FIG. 8, in which the distal end of tube 114 engages shoulder 95 sleeve 82. Delivery system 110 is now ready to install suture collet 10 in the body.

Figure 8A:
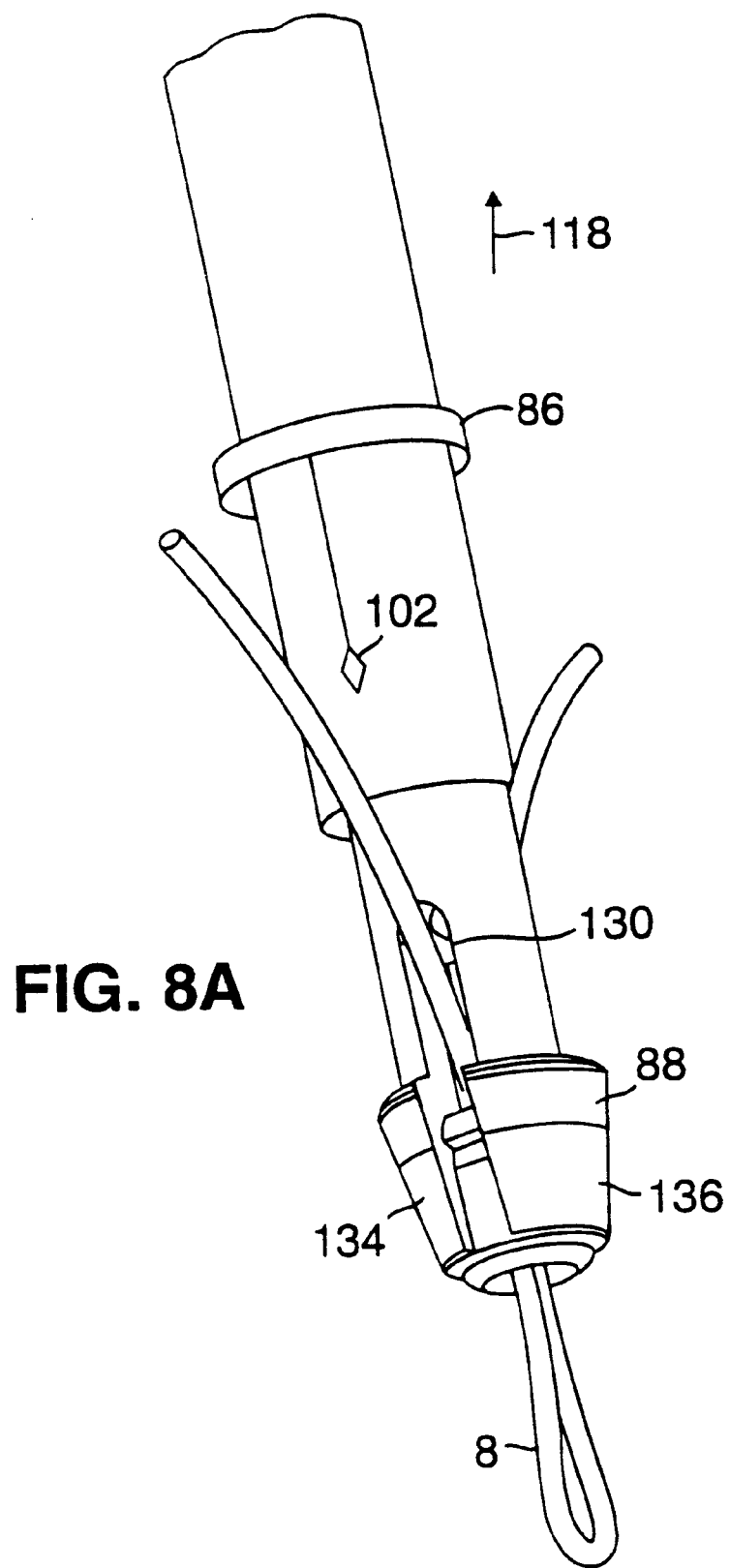
Figure 8B:
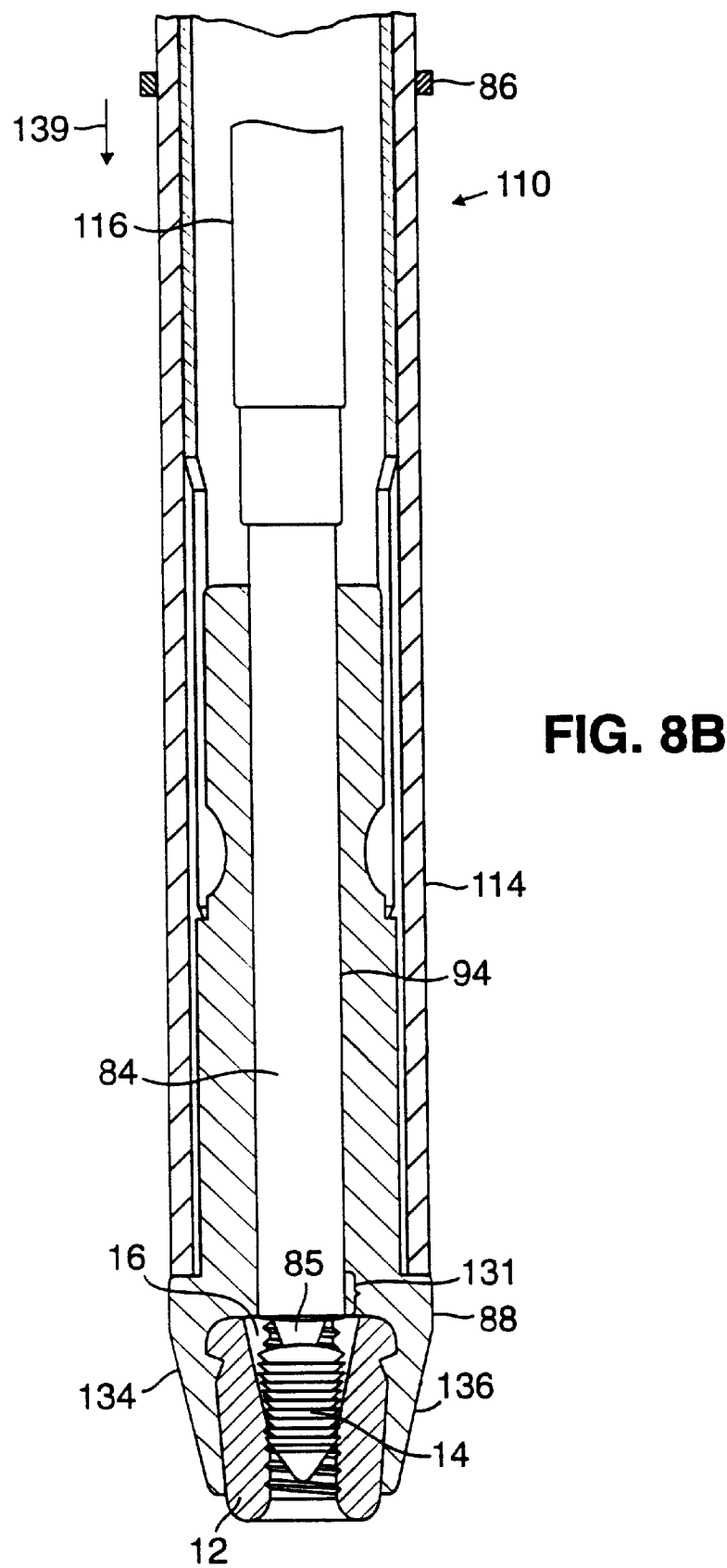
Figure 8C:
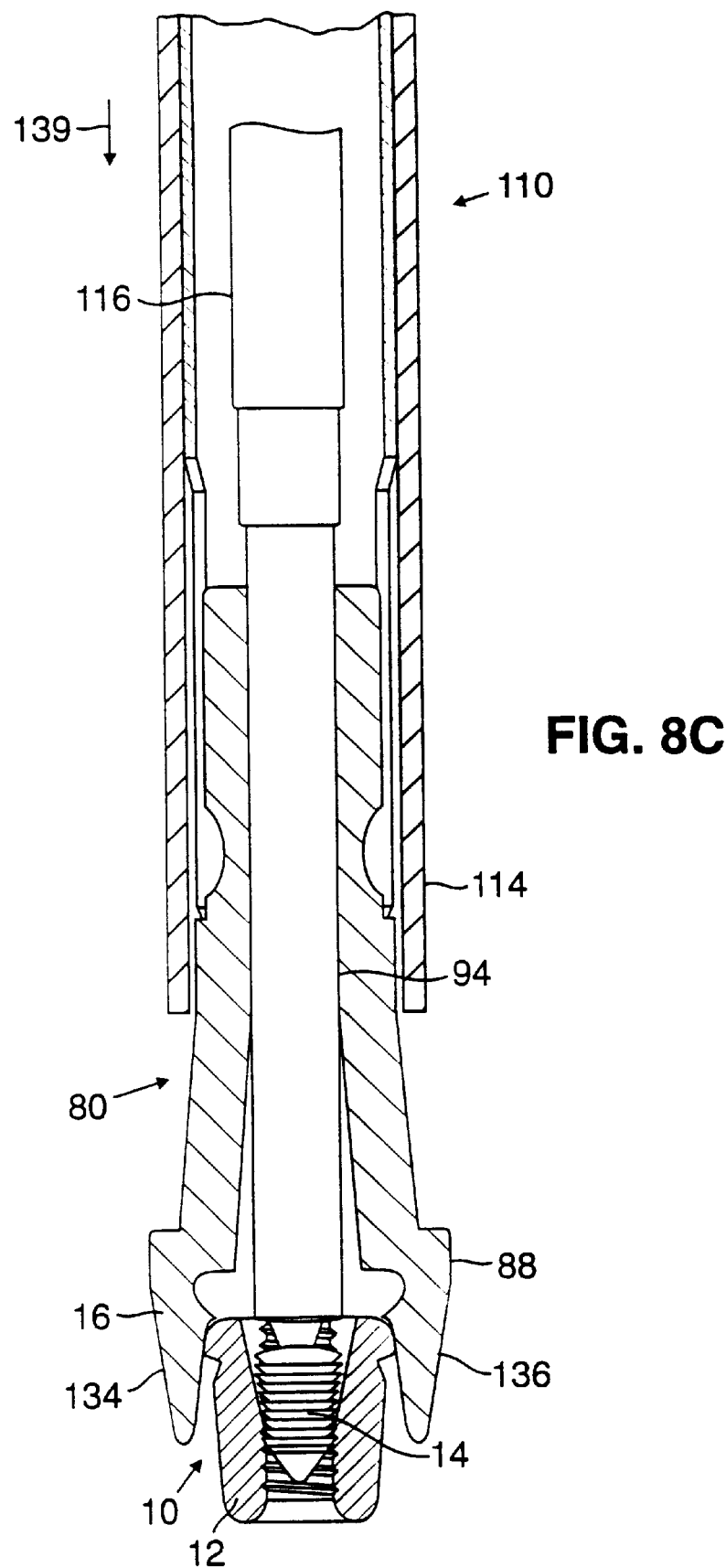

Referring also to FIGS. 8A–8C, suture collet 10 is emplaced with delivery system 110 as follows. For example, as a preliminary step, suture 8 can be mounted to bone 4 with anchor 6 and tied through ligament 2 (FIG. 1). The user then passes the ends of suture 8 (which may now be positioned inside or outside of the body) through threading loops 102, 104 (FIG. 7) and retracts outer tube 114 to expose slots 130, 132 (FIG. 8A). Next, suture threader collar 86 is moved proximally (arrow 118) to pull the ends of suture 8 through suture collet ring 12, passage 94, and slots 130, 132. Outer tube 114 is then allowed to return to its extended position against clamp 88. Delivery system 110 is then advanced, for example, through a conventional trocar used in arthroscopic or laproscopic surgery, to the fixation site.

Referring to FIG. 8B, delivery system 110 is maneuvered at the surgical site to position suture collet ring 12 as desired (e.g., against the upper surface of ligament 2, FIG. 1). Note that in the configuration shown, outer tube 114 envelopes all but the distal ends of clamping arms 134, 136, thereby holding them securely in place against suture collet ring 12. The user then advances actuator 116 distally (along arrow 139), thereby driving plunger 84 distally to slide pin 14 axially into bore 16 of locking ring 12. As discussed above, the insertion of pin 14 securely clamps suture 8 within suture receiving openings 52, 53. Tube 114 holds suture collet ring 12 securely in place while pin 14 is being inserted. (Note that with tube 114 extended, suture 8 exits slots 130 and 132 in distal regions 131 exposed by tube 114.)

Referring to FIG. 8C, the assembled suture collet 10 is removed from cartridge 80 simply by retracting outer tube 114 proximally to unsheathe clamp 88, advancing actuator 116 further distally, thereby driving plunger 84 further distally which pushes suture collet 10 distally releasing the suture collet from cartridge 80, followed by pulling the delivery system proximally as a unit. The retraction of outer tube 114 permits clamping arms 134, 136 to flex outwardly.

Note that the placement of suture 8 within ring 12 acts as the first throw of the suture knot to reduce the tissue and allows sliding travel of the suture much like the first throw of a conventional knot. The frictionless contact between ring 12 and the suture permits the surgeon to feel how much tension is being put into the tissue even more precisely than the first throw of a conventional knot which has some friction. This is particularly advantageous when suturing vessels with thin walls or suturing delicate tissue. In addition, the tension on the suture, instead of acting to pull the suture loose, increases the holding force on the suture applied by suture collet 10.

Figure 9:
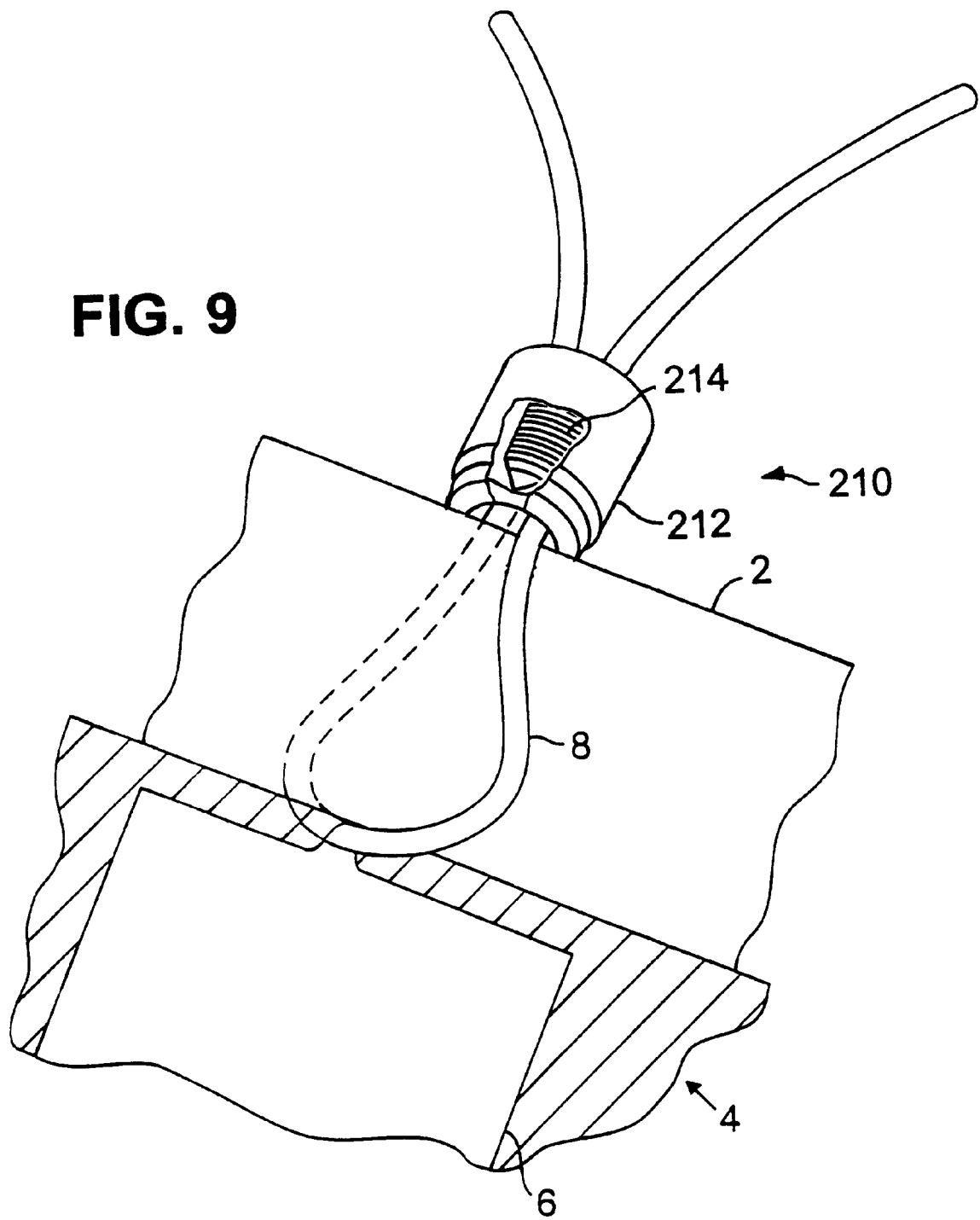
FIG. 9 shows an additional embodiment of a suture collet for securing suture.

Referring to FIG. 9, in a preferred embodiment, a suture collet 210 includes an outer locking ring 212 and an inner locking pin 214 which securely fasten suture 8 in place when pin 214 is inserted into ring 212.

Figure 10:
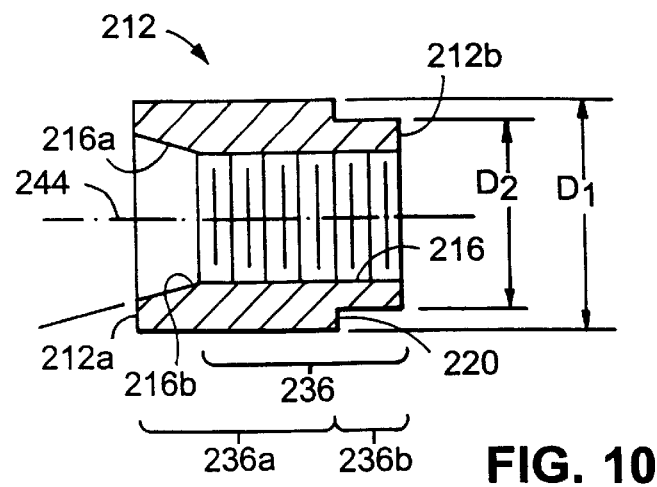
FIG. 10 is a cross-sectional view of an outer member of the suture collet of FIG. 9.

Referring to FIG. 10, ring 212 includes an axially-oriented cylindrical bore 216. A portion of the interior surface of ring 212 which defines bore 216 is threaded 236. Bore 216 extends completely through ring 212, from proximal end 212*a* to distal end 212*b*, along a longitudinal central axis 244 of ring 212. Bore 216 is tapered 216a from a larger diameter at proximal end 212a to a smaller diameter where threads 236 begin at 216b. Ring 212 has an outer diameter, $D_1$, of 0.123 inches over the majority 236a of its length, and a smaller outer diameter, $D_2$, of 0.105 inches over the remainder 236b of it length. A circumferential ledge 220 is located at the junction of diameters $D_1$ and $D_2$.

Figure 11:
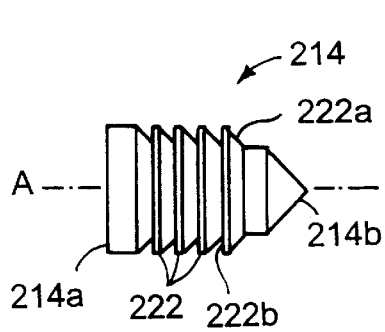
FIG. 11 is a side view of an inner member of the suture collet of FIG. 9.

Referring to FIG. 11, pin 214 is generally cylindrical in shape and is sized to enter bore 216. A portion of the exterior surface of pin 214 includes a series of axially spaced ridges 222 for lockingly engaging ring threads 236 in a ratchet-like manner when pin 214 is progressively inserted into bore 216 thus securing pin 214 in any one of a plurality of locked positions in ring 212 to secure suture 8 between ring 212 and pin 214.

The circumferentially oriented ridges 222 of pin 214 are axially spaced along pin 214 between proximal end 214a and distal end 214b. The leading (distal) surfaces 222a of ridges 222 are inclined (e.g., at 45 degrees) relative to a long axis A of pin 214 to slide past threads 236 of ring 212 during insertion, and the trailing (proximal) surfaces 222b of ridges 222 are oriented perpendicular to long axis A to lockingly engaging threads 236 when pin 214 has been inserted by the desired amount. Distal end 214b of pin 214 is conically shaped to help guide pin 214 into bore 216.

Figure 12:
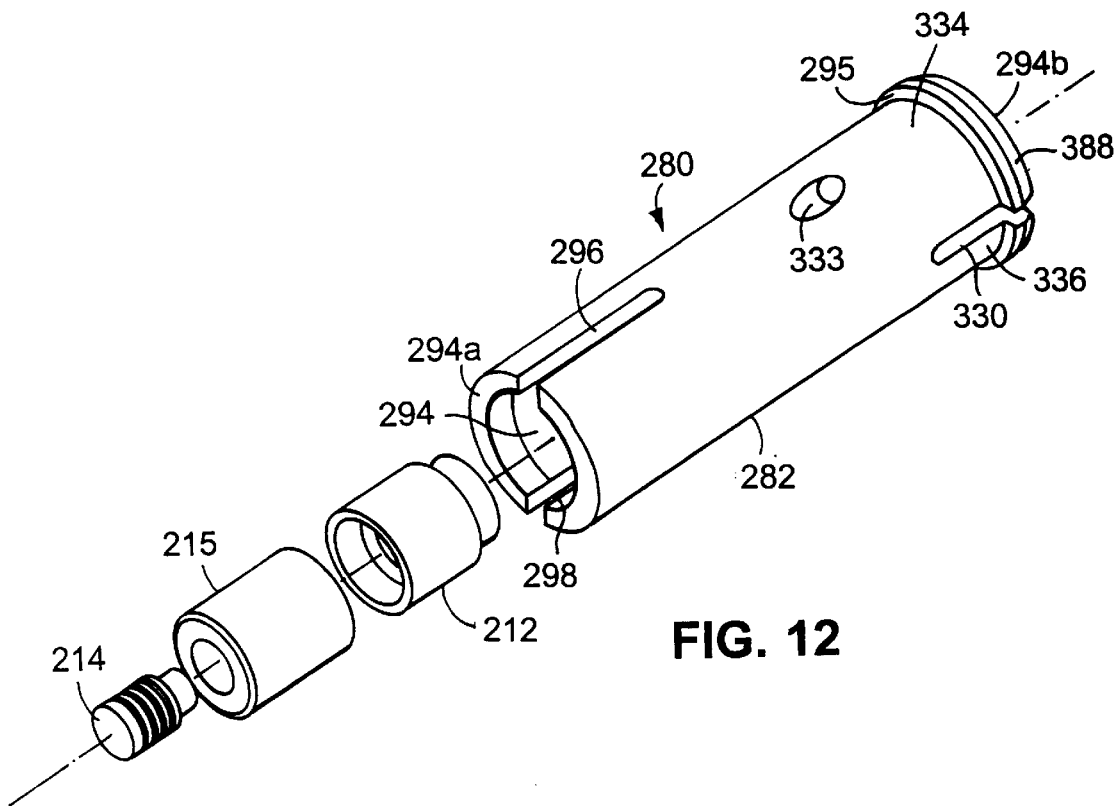
FIG. 12 is an exploded perspective view of a cartridge and the suture collet of FIG. 9.
Figure 13:
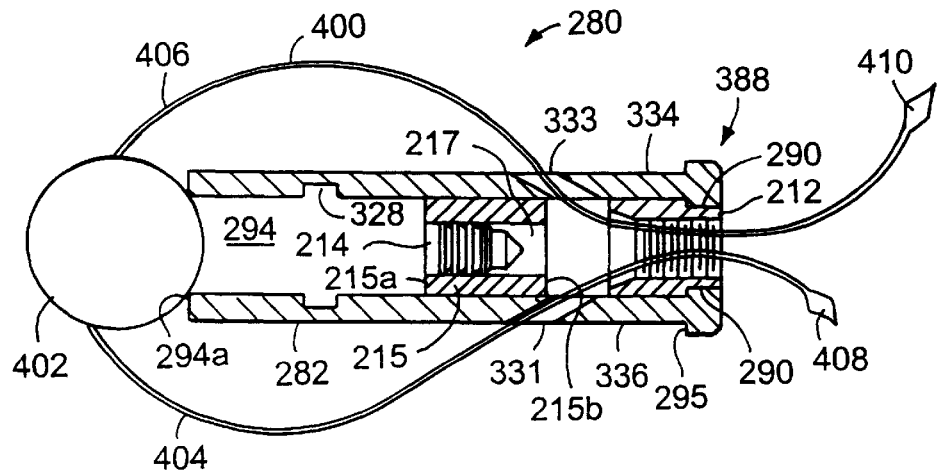
FIG. 13 is a cross-sectional view of the cartridge of FIG. 12 pre-loaded with the suture collet of FIG. 9.

Referring to FIGS. 12 and 13, to aid in the placement of suture collet 210, a cartridge 280 carries ring 212 and pin 214 and couples to a drive tool, described below, which inserts pin 214 into ring 212. Cartridge 280 includes a hollow sleeve 282 with an axial passage 294 extending completely through sleeve 282, from proximal end 294a to distal end 294b. The distal end 294b of sleeve 282 is provided with a pair of axial slots 330 (only one slot being shown) to define a pair of resilient arms 334, 336 which form a clamp 388 to hold suture collet ring 212 in place therebetween. Interior lips 290 on arms 334, 336 form a close fit against the smaller diameter region 236b of ring 212.

Sleeve 282 has proximal slots 296, 298, inclined apertures 331, 333, and a circumferential groove 328 in inner wall 282a of sleeve 282 for purposes to be described. A distal end of arms 334, 336 has an enlarged outer diameter relative to that of the remainder of sleeve 282, such that a shoulder 295 is defined, also for purposes to be discussed.

Pin 214 is supported within passage 294 by a carrier 215. Pin 214 is located within an opening 217 in carrier 215 extending from a proximal end 215a of carrier 215 to a distal end 215b. Carrier 215 acts to center pin 214 within cartridge passage 294.

A suture threader 400 is used to thread suture through ring 212 during operation. A proximal cap 402 is connected to the proximal ends of a pair of suture threader wires 404, 406 which respectively pass through apertures 331, 333 and into passage 294. The free ends of wires 404, 406 pass through bore 216 of suture collet ring 212 and terminate in a pair of threading loops 408, 410 respectively.

To assemble the cartridge assembly of FIG. 13, ring 212 is first placed within passage 294 and slid forward so that ledge 220 engages lips 290. Wires 404, 406 of suture threader 400 are passed through apertures 331, 333 and through ring bore 216. Pin 214 is then placed within carrier 215 and carrier 215 with pin 214 are together placed within passage 294 and positioned just proximally of ring 212.

Figure 14:
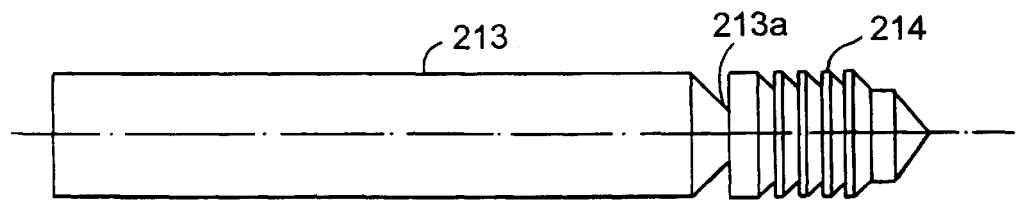
FIG. 14 is a side view of the inner member of FIG. 11 shown with an attached extension.

Referring to FIG. 14, to assist in the handling of pin 214, a proximal extension 213 (not shown in FIGS. 11 and 12) is formed on pin 214 which tapers distally to a small neck 213a at proximal end 214a of pin 214. Neck 213a permits proximal extension 213 to be easily broken off of pin 214 after pin 214 is inserted in carrier 215. With ring 212, pin 214, and carrier 215 in place, cap 402 of suture threader 400 is placed over passage opening 294a to contain the ring, pin and carrier within passage 294. Alternatively, cap 402 can be sized to fit within passage 294 to plug proximal end 294a of cartridge 280.

Figure 15:
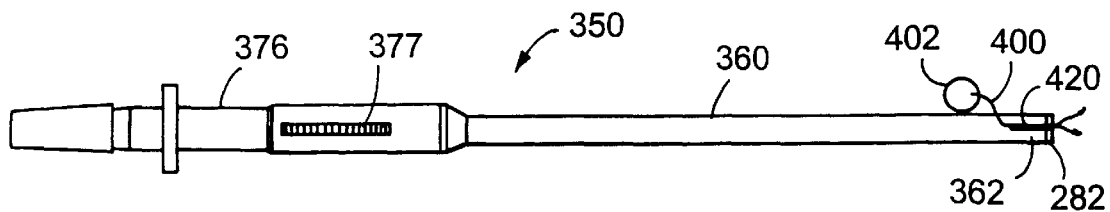
FIG. 15 shows a drive tool for use with the suture collet of FIG. 9.

FIG. 15 illustrates a drive instrument 350 which can be used to emplace suture collet 210 in the body and insert pin 214 into ring 212 to clamp suture in place in the manner discussed above.

Referring also to FIG. 16, instrument 350 has an outer sheath 360 which fits over sleeve 282. A distal end 362 of outer sheath 360 engages shoulder 295 of sleeve 282. Outer sheath 360 includes axial slots 420, 422 aligned with apertures 331, 333 for passage of suture 8. A grasper 364 of instrument 350 has a circumferential groove 366 with a distal ridge 370 configured to fit within groove 328 of sleeve 282, and a shoulder 373 which engages proximal end 294a of sleeve 282 to secure cartridge 280 within instrument 350.

A plunger 376 is slidable within grasper 364 and has a smaller diameter extension 378 which fits within carrier 215 to engage pin 214 and progressively insert pin 214 into passage 216 of ring 212. A spring (not shown) biases plunger 376 away from engagement with pin 214. A second spring 377 acts to bias outer sheath 360 toward engagement with shoulder 295. Alternatively, a position locking mechanism (not shown) can serve to lock outer sheath 360 in position against shoulder 295. Carrier 215 acts to center pin 214 such that plunger 376 squarely engages pin 214.

Cartridge 280 with ring 212, pin 214, carrier 215, and suture threader 400 preinstalled as described above, is inserted into instrument 350 by retracting outer tube 360 proximally (in the direction of arrow 318) to expose grasper groove 366. Cartridge 280, with cap 402 moved aside to expose passage 294, is then inserted onto grasper 364 until distal ridge 370 reaches and snap fits within groove 328. Proximal slots 296, 298 in sleeve 282 permit proximal end 294a of sleeve 282 to widen during insertion of grasper 364. Outer tube 360 is then returned to the position shown in FIG. 16 with spring 377 acting to maintain engagement of distal end 362 of tube 360 with shoulder 295 of sleeve 282. Instrument 350 is now ready to install suture collet 210 in the body.

Suture collet 210 is emplaced in the body with cartridge 280 and drive instrument 350 as follows. For example, as a preliminary step, suture 8 can be mounted to bone 4 with anchor 6 and passed through ligament 2 (FIG. 9). The user then passes the ends of suture 8 (which may now be positioned inside or outside of the body) through threading loops 408, 410. Next, suture threader 400 is moved proximally (arrow 318) using cap 402 to pull the ends of suture 8 through suture collet ring 212, apertures 331, 333 and slots 420, 422. Instrument 350 is then advanced, for example, through a conventional trocar used in arthroscopic or laproscopic surgery, to the fixation site.

Referring to FIG. 16A, instrument 350 is maneuvered at the surgical site to position suture collet ring 212 as desired (e.g., against the upper surface of ligament 2, FIG. 9). Note that in the configuration shown, outer tube 360 envelopes all but the distal ends of clamping arms 334, 336, thereby holding them securely in place against suture collet ring 212. The user then advances plunger 376 distally (along arrow 339), thereby driving plunger extension 378 distally. Plunger 376 acts to initially slide carrier 215 with pin 214 distally. When carrier 215 contacts ring 212, carrier 215 stops while plunger extension 378 continues to move distally, thereby progressively inserting pin 214 axially into bore 216 of ring 212. Tube 360 holds cartridge 280 securely in place while pin 214 is being inserted. Pin 214 is progressively inserted into bore 216 until pin 214 reaches a desired locked position in ring 212 securing suture 8 between ring 212 and pin 214.

Figure 16B:
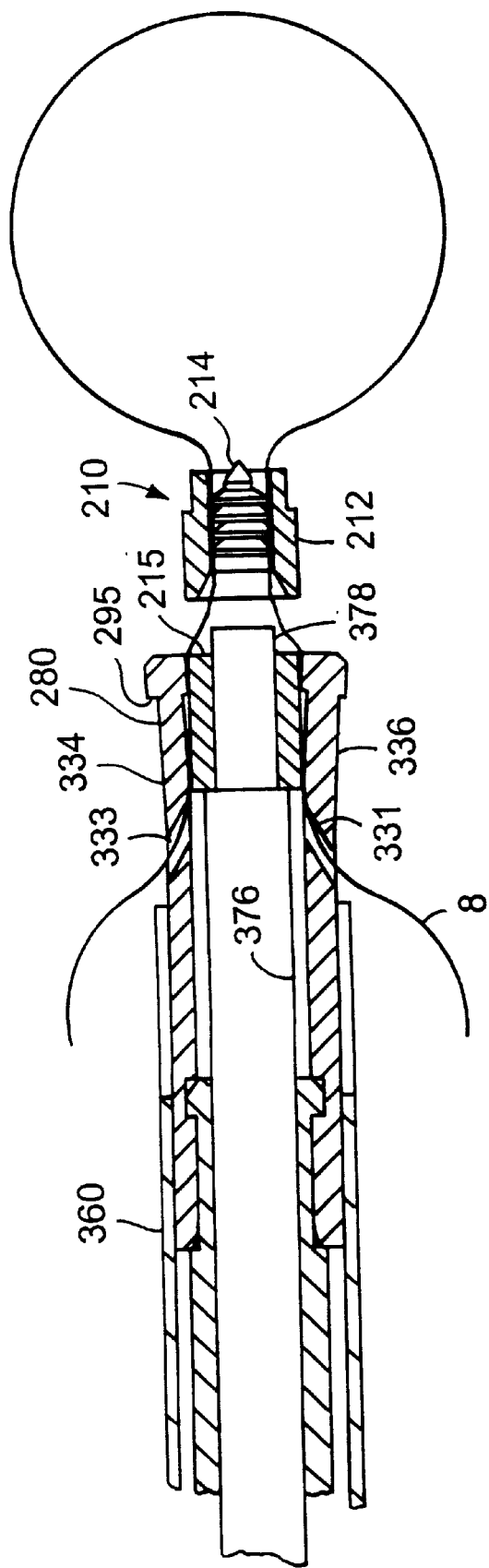

Referring to FIG. 16B, the assembled suture collet 210 is removed from cartridge 280 simply by retracting tube 360 axially away from shoulder 295 and advancing plunger 376 further distally. With tube 360 retracted, arms 334, 336 of cartridge 280 flex outwardly as suture collet 210 is moved distally thereby permitting extension 378 to push suture collet 210 distally from cartridge 280. The distance that plunger 376 can be moved distally is limited by travel stops or limits (not shown) such that carrier 215 is not also pushed from cartridge 280.

Other embodiments are within the scope of the following claims.

Figure 17:
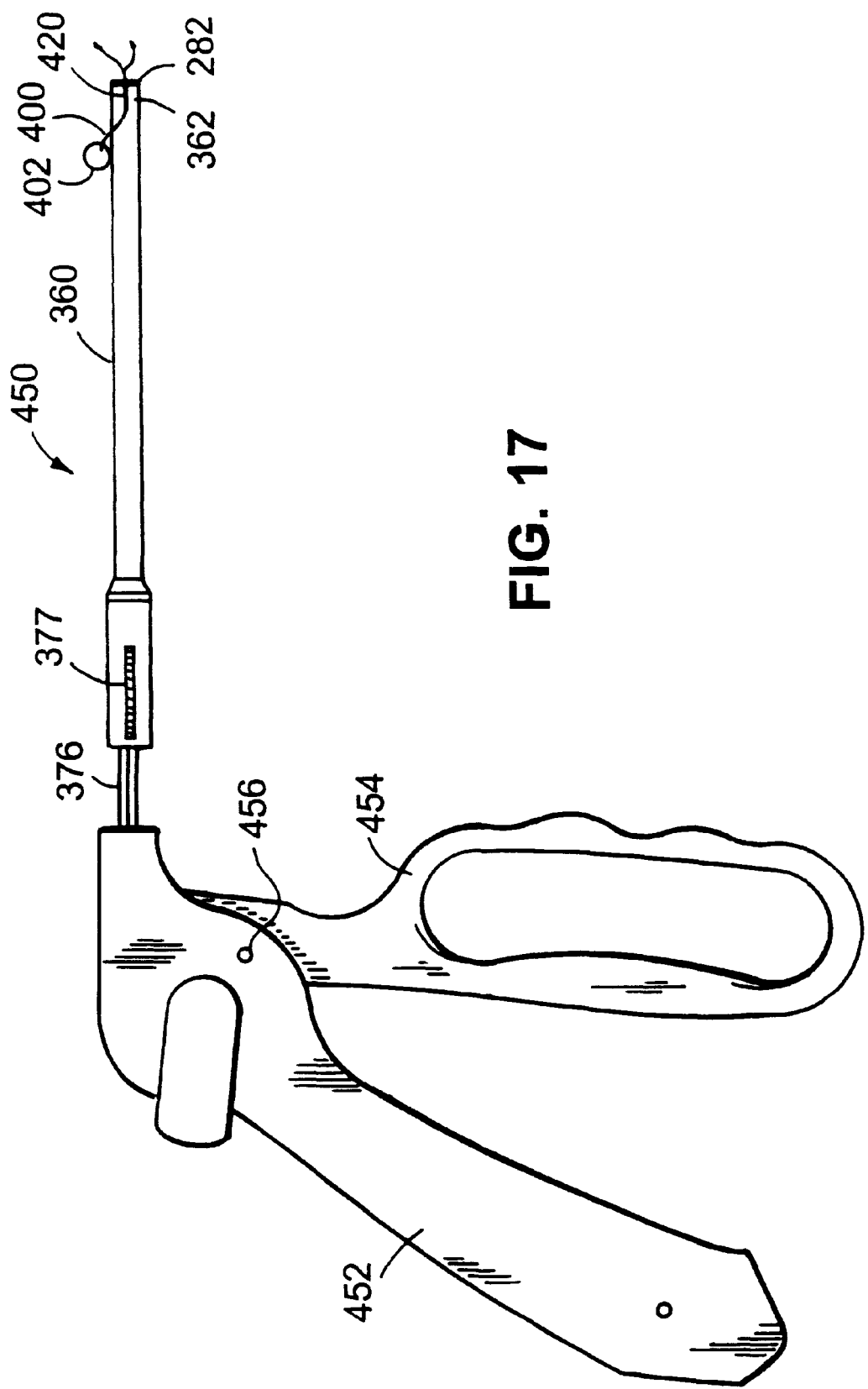
FIG. 17 is a side view of an alternative embodiment of a drive tool.

For example, referring to FIG. 17, in a preferred embodiment, drive instrument 450 includes a handle 452 and a trigger 454 pivotably mounted to handle 452 about pivot pin 456. Plunger 376 is snapped into or permanently mounted to handle 452 and linked to trigger 454 such that movement of trigger 454 controls the movement of plunger 376. Outer sheath 360, grasper 364 and plunger 376 act as described above with reference to drive instrument 350.

The tunnels of ring 12 and pin 14 can be inclined at other angles, as desired. In fact, a surface of only one of these members can be inclined (i.e., the corresponding surface of the other member can be parallel to the longitudinal axis of the collet).

The relative positions of suture receiving openings 52, 53 can be changed as desired. For example, openings 52, 53 can be positioned adjacent to each other. More or fewer suture receiving openings can be provided, as desired.

Plunger 84 and pin 14 can be manufactured as one unit. After the pin is inserted into the ring, rotation of plunger 84 would dislodge the pin from the plunger. Plunger 84 can include a distal cam surface such that rotation of the plunger acts to force arms 134, 136 apart to facilitate removal of the suture collet from cartridge 80.

Suture collets 10 and 210 can be used wherever a suture knot would be tied, for example, in ligating branches of vessels, in soft-tissue repair, in reducing tissues, and in securing other types of tissue to bone.

Ring 12 and pin 14 and ring 212 and pin 214 can be connected in other ways. For example, in the ratcheting technique discussed herein, pin 214 may be threaded and ring 212 can include ridges 222. A single ridge 222 can be used in place of the axially spaced series of ridges discussed above.

The suture collet members need not be insertable one into the other, and they can be connected together in other ways (such as by rotating one member with respect to the other). In a rotating embodiment, the clamping surfaces should be inclined with respect to the direction of rotation to provide the mechanical advantage discussed above. An inner pin can be positioned first and an outer ring can be driven over the inner pin.

Other materials can be used according to the suturing application.

What is claimed is:

1. A suture securing device, comprising:
   an outer member including a suture receiving passage extending therethrough between an open proximal end of the outer member and an open distal end of the outer member, said outer member including a first locking element, and
   an inner member configured for distal insertion within said suture receiving passage, said inner member including a second locking element, said first and second locking elements configured to lockingly engage each other at a plurality of positions along a longitudinal axis of said passage to lock said inner member to said outer member at a selected one of said positions such that said inner member resists movement proximally relative to said outer member,
   said inner member and said outer member constructed to secure a suture therebetween.

2. The suture securing device of claim 1 wherein said first locking element comprises a threaded portion of said suture receiving passage, and said second locking element comprises a ridge for engagement with said threaded portion.

3. The suture securing device of claim 2 wherein said second locking element comprises a plurality of ridges for engagement with said threads of said outer member.

4. The suture securing device of claim 2 wherein said inner member defines a long axis and a distal surface of said ridge is inclined relative to said long axis to slide past said threads during insertion, and a proximal surface of said ridge is oriented perpendicular to said long axis to lockingly engaging said threads when said inner member has been inserted within said suture receiving passage by a desired amount.

5. The suture securing device of claim 1 wherein a proximal end of said suture receiving passage tapers distally from a wider diameter to a smaller diameter, and a distal end of said inner member is conically shaped, said taper and said conical shape for aiding in the insertion of said inner member within said suture receiving passage.

6. The suture securing device of claim 1 wherein said inner member is configured for progressive insertion within said suture receiving passage and engagement with said outer member in any one of a plurality of locked positions.

7. The suture securing device of claim 1 wherein said suture receiving passage is further defined by an outer surface of said inner member and an inner surface of said outer member, one of said surfaces being inclined relative to a longitudinal axis of said device to progressively constrict said opening when said inner member is inserted within said outer member.

8. The suture securing device of claim 7 wherein said surfaces of both said inner member and said outer member are inclined with respect to said axis.

9. A suture securing cartridge, comprising:
   a sleeve having an axial bore, and
   a suture securing device including an outer member at least a portion of which is disposed within said bore at a distal region of said sleeve, and an inner member disposed within said bore proximally of said outer member and configured for insertion into a suture receiving passage in said outer member,
   said distal end of said sleeve including a flexible member which flexes outward to permit release of said outer member from said bore.

10. The suture securing cartridge of claim 9, further including a carrier disposed in said bore proximally of said outer member, said carrier engaging said inner member to align said inner member with said suture receiving passage.

11. The suture securing cartridge of claim 10 wherein said carrier defines an opening and said inner member is disposed in said opening.

12. The suture securing cartridge of claim 9 wherein a proximal end of said sleeve is configured to receive an actuator for moving said inner member into said suture receiving passage.

13. The suture securing cartridge of claim 9 wherein said sleeve has a distal clamp for selectively preventing said outer member from exiting said bore in a distal direction.

14. The suture securing cartridge of claim 13 wherein said flexible member comprises a resilient arm of said distal clamp which is outwardly flexible to permit said outer member to exit said bore in the distal direction.

15. The suture securing cartridge of claim 9 wherein said sleeve includes an inclined aperture extending through a wall of said sleeve and a suture threader extending through said inclined aperture and through said suture receiving passage.

16. The suture securing cartridge of claim 15 wherein said suture threader includes a cap covering an open end of said bore at a proximal end of said sleeve.

17. A suturing apparatus comprising:
   a suture securing cartridge that includes
      a sleeve having an axial bore, and
      a suture securing device including an outer member at least a portion of which is disposed within said bore at a distal region of said sleeve and an inner member disposed within said bore proximally of said outer member and configured for insertion into a suture receiving passage in said outer member, and
   a drive tool that includes
      an outer sheath which fits over said sleeve, an intermediate tube which engages said sleeve to secure said cartridge to said drive tool, and a movable element located within said intermediate tube for progressively inserting said inner member into said passage of said outer member.

18. The suturing apparatus of claim 17 wherein said sleeve has a circumferential groove in said bore, and said intermediate tube has a grasper which engages said groove to secure said cartridge to said drive tool.

19. A method of securing a suture, comprising:
   threading a suture through an open distal end of a passage in an outer member, said outer member including a first locking element, and
   distally inserting an inner member into said outer member, said inner member including a second locking element for engaging said first locking element to lock said inner member to said outer member such that said inner member resists movement proximally relative to said outer member to secure the suture between said inner member and said outer member.

20. A method of using a suture securing device, comprising:
   providing a preassembled suture securing cartridge including a sleeve having an axial bore and a suture securing device, said suture securing device including an outer member at least a portion of which is disposed within said bore at a distal region of said sleeve and an inner member disposed for insertion into a suture receiving passage in said outer member,
   inserting said preassembled cartridge into a drive tool that includes an outer sheath which fits over said sleeve, an intermediate tube which engages said sleeve to secure said cartridge to said drive tool, and a movable element located within said intermediate tube for progressively inserting said inner member into said passage of said outer member, and
   advancing said movable element to progressively insert said inner member into said passage.

21. A suture securing cartridge, comprising:
   a sleeve having an axial bore and two slots extending proximally from a distal end of said sleeve such that the distal end of said sleeve defines a pair of resilient arms, and
   a suture securing device including an outer member disposed in said bore at a distal region of said sleeve and an inner member disposed in said bore proximally of said outer member and configured for insertion into a suture receiving passage in said outer member,
   said resilient arms engaging said outer member to selectively prevent said outer member from exiting said bore in a distal direction and said resilient arms being outwardly flexible to permit said outer member to exit said bore in a distal direction.

22. A suture securing cartridge, comprising:
   a sleeve having an axial bore and an inclined aperture extending through a wall of said sleeve,
   a suture securing device including an outer member disposed in said bore at a distal region of said sleeve and an inner member disposed in said bore proximally of said outer member and configured for insertion in to a suture receiving passage in said outer member, and
   a suture threader extending through said inclined aperture and through said suture receiving passage.

23. The suture securing cartridge of claim 22 wherein said suture threader includes a cap covering an open end of said bore at a proximal end of said sleeve.

24. A suture securing cartridge, comprising:
   a sleeve having an inner wall defining a bore,
   and a suture securing device at least partially disposed within said bore, said suture securing device including
      an outer member having a suture receiving passage, said outer member including a first locking element, and
      an inner member configured for distal insertion within said suture receiving passage, said inner member including a second locking element for engaging said first locking element to lock said inner member to said outer member such that said inner member resists movement proximally relative to said outer member, said inner member and said outer member constructed to secure a suture therebetween.

25. A suture securing cartridge, comprising:
   a sleeve having an inner wall defining an axial bore, and
   a suture securing device including an outer member at least a portion of which is disposed within said bore at a distal region of said sleeve, and an inner member disposed within said bore proximally of said outer member and configured for insertion into a suture receiving passage in said outer member to secure a suture between said outer member and said inner member, said sleeve being configured to permit said suture securing device to be distally expelled from said axial bore.

26. The suture securing cartridge of claim 25 wherein said outer member and said inner member are sized such that said inner member fits entirely within said suture receiving passage.

27. A suture securing cartridge, comprising:
   a sleeve having an axial bore, and
   a suture securing device including an outer member at least a portion of which is disposed within said bore at a distal region of said sleeve, and an inner member disposed within said bore proximally of said outer member and configured for insertion into a suture receiving passage in said outer member, said sleeve including two slots extending proximally from a distal end of said sleeve such that the distal end of said sleeve defines a pair of resilient arms, said resilient arms engaging said outer member to selectively prevent said outer member from exiting said bore in a distal direction and said resilient arms being outwardly flexible to permit said outer member to exit said bore in a distal direction.

28. A suture securing cartridge, comprising:

a sleeve having an axial bore, and a suture securing device including an outer member at least a portion of which is disposed within said bore at a distal region of said sleeve, and an inner member disposed within said bore proximally of said outer member and configured for insertion into a suture receiving passage in said outer member, said sleeve including an inclined aperture extending through a wall of said sleeve and a suture threader extending through said inclined aperture and through said suture receiving passage.

29. The suture securing cartridge of claim 28 wherein said suture threader includes a cap covering an open end of said bore at a proximal end of said sleeve.

30. A suture securing device, comprising:

an outer member including a suture receiving passage, a proximal portion of said suture receiving passage tapering distally from a wider diameter to a smaller diameter, a portion of said passage distal of said proximal portion having a constant diameter, said outer member including a first locking element, and an inner member configured for distal insertion within said suture receiving passage, a distal end of said inner member being conically shaped, said tapering and said conical shape for aiding in the insertion of said inner member within said suture receiving passage, said inner member including a second locking element for engaging said first locking element to lock said inner member to said outer member such that said inner member resists movement proximally relative to said outer member, said inner member and said outer member constructed to secure a suture therebetween.

31. A suture securing device, comprising:

an outer member including a suture receiving passage, said outer member including a first locking element, and an inner member configured for distal insertion within said suture receiving passage, said inner member including a second locking element for engaging said first locking element to lock said inner member to said outer member such that said inner member resists movement proximally relative to said outer member, said inner member and said outer member constructed to secure a suture therebetween, said suture receiving passage being further defined by an outer surface of said inner member and an inner surface of said outer member, one of said surfaces being inclined relative to a longitudinal axis of said device to progressively constrict said opening when said inner member is inserted within said outer member.

32. The suture securing device of claim 31 wherein said surfaces of both said inner member and said outer member are inclined with respect to said axis.

33. A suture securing device for replacing suture knotting in a surgical procedure, comprising:

an outer member including a suture receiving passage extending therethrough between an open proximal end of the outer member and an open distal end of the outer member, a portion of said suture receiving passage having a constant diameter, said outer member including a first locking element, and an inner member configured for distal insertion within said suture receiving passage, said inner member including a second locking element for engaging said first locking element to lock said inner member to said outer member such that said inner member resists movement proximally relative to said outer member, said inner member and said outer member when locked together having a size which enables said inner member and said outer member to remain in-situ after the surgical procedure and being constructed to secure a suture therebetween, thereby to provide a replacement for knotting as a way to secure the suture.

34. A suture securing device for replacing suture knotting in a surgical procedure, comprising:

an outer member including an inner wall defining a suture receiving passage extending therethrough between an open proximal end of the outer member and an open distal end of the outer member, said outer member including a first locking element, and an inner member configured for distal insertion within said suture receiving passage, said inner member having an outer surface configured to provide continuous circumferential contact with said passage wall, said inner member including a second locking element for engaging said first locking element to lock said inner member to said outer member such that said inner member resists movement proximally relative to said outer member, said inner member and said outer member when locked together having a size which enables said inner member and said outer member to remain in-situ after the surgical procedure and being constructed to secure a suture therebetween, thereby to provide a replacement for knotting as a way to secure the suture.

* * * * *